United States Patent [19]

Scheben

[11] Patent Number: 4,980,501

[45] Date of Patent: Dec. 25, 1990

[54] PRODUCTION OF SECONDARY-BUTYL FLUOROESTER AND SECONDARY-BUTYL ALCOHOL OBTAINED THEREFROM

[75] Inventor: John A. Scheben, Erlanger, Ky.

[73] Assignee: National Distillers and Chemical Corporation, New York, N.Y.

[21] Appl. No.: 523,585

[22] Filed: Mar. 19, 1990

Related U.S. Application Data

[63] Continuation of Ser. No. 635,087, Jul. 27, 1984, abandoned.

[51] Int. Cl.$^5$ .................................................. C07C 69/63
[52] U.S. Cl. .................................. 560/227; 560/219; 560/192; 560/125; 560/103; 560/83
[58] Field of Search ............... 560/227, 219, 192, 125, 560/103, 83

[56] References Cited

U.S. PATENT DOCUMENTS 2,858,331  10/1958  Fenske et al. ................... 560/192
4,281,176  7/1981  Gruffaz et al. ................... 560/103

OTHER PUBLICATIONS

Hamaya, *chemical Abstracts*, vol. 98, No. 1612265 (1983).
Billmeyer, *Textbook of Polymer Science*, (Interscience, N.Y., 1962), pp. 293–295.

*Primary Examiner*—Bruce Gray
*Attorney, Agent, or Firm*—Kenneth D. Tremain; Gerald A. Baracka

[57] ABSTRACT

A process for the production of secondary-butyl perfluoroester is provided by reacting ethylene with a perfluorocarboxylic acid in the presence of oxygen.

5 Claims, No Drawings

PRODUCTION OF SECONDARY-BUTYL FLUOROESTER AND SECONDARY-BUTYL ALCOHOL OBTAINED THEREFROM

This is a continuation of patent application Ser. No. 06/635,087, filed July 27, 1984 now abandoned.

This invention relates to the production of secondary-butyl fluoroester from ethylene and a perfluorocarboxylic acid. Additionally, the invention is directed to a novel and unique method of producing secondary-butyl alcohol from the secondary-butyl fluoroester produced from ethylene and a perfluorocarboxylic acid in the presence of oxygen.

BACKGROUND OF THE INVENTION

There are only a few known processes available for the production of secondary-butyl alcohol. Secondary-butyl alcohol is known to be produced from a $C_4$ hydrocarbon stream from which butadiene and isobutylene have been extracted. The remaining butane-butylene stream is reacted with sulfuric acid and the resulting sulfates are hydrolyzed by water to yield the alcohol and sulfuric acid. Overall conversion is about 84 percent with 0.9 pound of butylenes consumed per pound of secondary-butanol produced. Another known technique is the direct hydration in the vapor phase by passing 1-butene and steam over a solid catalyst containing phosphoric acid and oxides of certain metals at 240° C. and 10 atmospheres pressure as described in U.S. Pat. No. 2,052,095 to Joshua, et al. Another process to produce secondary-butyl alcohol is by fermentation.

British Patent No. 776,073 to Esso Research and Engineering Company describes the esterification of olefins, especially ethylene, with a fluorinated carboxylic acid in the presence of sulfuric acid to produce a saturated alkyl ester of the fluorinated carboxylic acid. For example, ethylene reacted with trifluoroacetic acid would produce ethyl trifluoroacetate acid and propylene reacted with trifluoroacetic acid would produce propyl trifluoroacetate. It should be noted that in the disclosure of the British Patent, that the same number of carbon atoms of the olefin are present in the alkyl portion of the resulting alkyl fluoroester.

SUMMARY OF THE INVENTION

It has now been discovered that secondary-butyl fluoroesters can be produced by the reaction of readily available ethylene with a perfluorocarboxylic acid in the presence of oxygen. The direct reaction of ethylene, in a dimerization reaction with a perfluorocarboxylic acid is not known nor recognized in the prior art. Additionally, secondary-butyl alcohol can be obtained in attractive yields by the direct hydrolysis or saponification of the secondary-butyl fluoroester produced by the process of this invention.

DETAILED DESCRIPTION OF INVENTION

According to the present invention, ethylene is reacted with a perfluorocarboxylic acid in the presence of oxygen to produce a secondary-butyl perfluoroester. The reaction is carried out at temperatures from about 75° C. to about 300° C., preferably about 100° C. to about 200° C., and pressures of autogenous pressure of ethylene to about 2000 psig. or higher, preferably about 500 to about 1000 psig. for a period of time until no ethylene is observed as reacting. The time of reaction can range from as little as a few seconds to as much as ten hours depending on the amounts of reactants.

The perfluorocarboxylic acids used in the process of this invention are those carboxylic acids having all hydrogen atoms other than the carboxyl hydrogens replaced by fluorine and particularly mono- or dicarboxylic perfluoroaliphatic acids with 2 to 6 carbon atoms per molecule. Useful perfluoroacids include trifluoroacetic, pentafluoropropionic, heptafluorobutyric and tetrafluorosuccinic acids as well as other fully fluorinated acids such as malonic, maleic, benzoic, phthalic and cyclohexanecarboxylic. The preferred perfluorocarboxylic is trifluoroacetic acid.

The amount of perfluorocarboxylic acid used is present in a molar ratio of acid to ethylene greater than 0.5/1 to about 20/1, preferably greater than 0.5/1 to about 10/1.

In accordance with the present invention, the presence of oxygen is necessary for the production of the secondary-butyl perfluoroesters although oxidation is not involved. Without oxygen present, satisfactory yields of secondary-butyl perfluoroesters are not obtained. The amount of oxygen employed in the process of this invention can range from about 0.0001 to about 20 mole percent of total gases present, preferably about 0.05 to about 10 mole percent of the total gases present. The oxygen can be present in its pure form or in oxygen-containing gases such as air, or oxygen mixed with inert gases such as nitrogen, carbon dioxide and the like. Oxygen-producing compounds in the form of organic or inorganic peroxides can be used. Suitable peroxides include hydrogen peroxide and organic peroxides including dibenzyl peroxide, dicumyl peroxide, ditertiary-butyl peroxide, peroxy esters including t-butyl-peroxybenzoate, t-butylperoxyoctoate, t-butylperoxy acetate, t-butylperoxy isobutyrate and t-butylperoxy-propanoate, and diacylperoxides including dilauroyl peroxide, dibenzyl peroxide, diacetyl peroxide, and the like.

Although metallic catalysts are not necessary to produce the secondary-butyl perfluoroesters of this invention, these catalysts may be used to increase the speed of the reaction and thereby shorten the reaction time. It has been found that the reactive metallic catalysts of Group VIII of the Periodic table such as palladium, platinum, ruthenium and the like, in catalytic amounts, can be used alone or on a catalyst support such as aluminum oxide. The preferred metallic catalyst is palladium.

The preparation of the secondary-butyl perfluoroesters in accordance with this invention can be carried out in any suitable pressure equipment such as stirred autoclaves or rocking units. The equipment may be constructed of any conventional material such as glass, steel, corrosion resistant stainless steel, etc. Metal reactors do not participate, influence, or significantly detrimentally affect the desired reaction.

In a further embodiment of the present invention, the secondary-butyl perfluoroesters prepared herein are converted to alcohol by hydrolysis, which includes acid hydrolysis, saponification or alcoholysis and the art known equivalents thereof. The hydrolysis can be carried out in the pressence of acid such as hydrochloric acid, sulfuric acid, etc., acid ion exchange resin in accordance with procedures which are well known in the art to provide secondary-butyl alcohol and perfluorocarboxylic acid. Standard distillation equipment can readily separate the alcohol from the perfluorocarboxylic acid which can be recycled to the original esterification reaction. Where saponification is used to convert the perfluoroester into alcohol, the latter may be recovered by distillation and the free perfluoroacid may be regenerated from remaining perfluoroacid salt by acidolysis or acidification with a strong acid such as sulfuric acid or hydrochloric acid. Finally the liberated acid may be recovered by distillation, liquid extraction using solvents such as ether or other appropriate procedures known to the art.

Among the applications for the secondary-butyl perfluoroesters prepared herein, such as secondary-butyl trifluoroacetate, is their use as selective solvents in the polymer field. Secondary-butyl alcohol obtained from secondary-butyl perfluoroesters, is mainly used for its conversion to methyl ethyl ketone, a well-known solvent. Other uses for secondary butyl alcohol include the manufacture of secondary-butyl acetate, fruit essences, perfumes, dye-stuffs, wetting agents, coupling agents for hydraulic brake fluids, and the like.

The following examples further illustrate the present invention.

EXAMPLES 1-8

In each of the examples, a 316-stainless steel pressure reactor having a 30 milliliter capacity, was shaken in a thermostated oven. In each example, 5 milliliters of trifluoroacetic acid (0.067 mol.) was added and ethylene, air or nitrogen added to the desired pressure. The conditions of the reaction and yields of secondary-butyl trifluoroacetate based on trifluoroacetic acid are shown in Table I below:

TABLE I

| | Production of Secondary-Butyl Trifluoroacetate | | | | | |
|---|---|---|---|---|---|---|
| | Pounds per Square Inch, Gauge | | | Reaction | Time | Yield |
| Example | Ethylene | Air | $N_2$ | temp, °C. | hrs. | % |
| 1 (a) | 500 | — | 300 | 150 | 1 | 88 |
| 2 | 500 | 300 | — | 150 | 1 | 81 |
| 3 | 500 | — | 300 | 150 | 1 | 25 |
| 4 (b) | 1000 | — | — | 75 | 9 | 0 |
| 5 (b) | 1000 | — | — | 150 | 1 | trace |
| 6 (b) | 1000 | — | — | 150 | 5 | 7 |
| 7 (b) | 500 | 300 | — | 150 | 4 | 67 |
| 8 (b) (c) | 500 | 300 | — | 150 | 4 | 58 |

(a) 0.19 gram of 1.2% Palladium on $Al_2O_3$ powder
(b) glass liner used in reactor
(c) Example 8 contained a small amount of stainless steel filings to determine the effect of the metal in the reaction.

EXAMPLE 9

Secondary-butyl trifluoroacetate, produced in each of the examples, 1 through 3 and 6 through 8 is hydrolyzed to secondary-butyl alcohol and trifluoroacetic acid. The hydrolysis is carried out under conditions of reflux, in the presence of aqueous hydrochloric acid for 60 minutes. The secondary-butyl alcohol produced is separated from the trifluoroacetic acid by distillation. The trifluoroacetic acid can be recycled to the initial reaction of trifluoroacetic acid and ethylene.

The nitrogen used in Examples 1 and 3 contains a small amount of oxygen (about 0.0001 mole %) which acts as a catalyst in the reaction of ethylene and trifluoroacetic acid. It should be noted that the use of a palladium catalyst in Example 1 produced good yields of secondary-butyl trifluoroacetate with an ethylene-nitrogen atmosphere. In Example 3, where nitrogen was used but no catalyst was present, a smaller yield of product was obtained. Good yields of ester were obtained in Example 2 where no catalyst was used but air was substituted for nitrogen. Similarly, in Examples 7 and 8 where no catalyst was present but the reaction occurred in the presence of air, satisfactory yields of secondary-butyl trifluoroacetate were obtained. In Examples 4, 5 and 6 where no oxygen or no catalyst was used, exceptionally poor yields of product were obtained either with extended reaction times (Examples 5 and 6) or increased reaction temperatures (Examples 4 and 6). Comparing Example 7 with Example 8 containing a small amount of stainless-steel filings, suggest that the stainless steel reaction walls have no effect on the ester yield.

What is claimed is:

1. A process for producing secondary-butyl perfluoroesters comprising reacting ethylene and a perfluorocarboxylic acid in the presence of oxygen and a Group VIII metallic catalyst at a pressure of 500 to 1,000 psig and temperature from about 100° C. to 200° C., the molar ratio of said perfluorocarboxylic acid to ethylene ranging from about 1:5:1 to 10:1.

2. The process of claim 1 wherein the amount of oxygen ranges from about 0.0001 to about 20 mole percent of the total gases present.

3. The process of claim 2 wherein the Group VIII metallic catalyst is selected from the group consisting of palladium, platinum and ruthenium.

4. The process of claim 3 wherein the perfluorocarboxylic acid is trifluoroacetic acid.

5. The process of claim 4 wherein the metallic catalyst is palladium.

* * * * *